(12) United States Patent
Casavant et al.

(10) Patent No.: US 7,904,157 B2
(45) Date of Patent: Mar. 8, 2011

(54) SELF LIMITED RATE RESPONSE

(75) Inventors: David A. Casavant, Reading, MA (US); Paul A. Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 798 days.

(21) Appl. No.: 11/764,368

(22) Filed: Jun. 18, 2007

(65) Prior Publication Data

US 2007/0299478 A1 Dec. 27, 2007

Related U.S. Application Data

(63) Continuation of application No. 10/971,686, filed on Oct. 25, 2004, now Pat. No. 7,248,924.

(51) Int. Cl.
*A61N 1/08* (2006.01)
(52) U.S. Cl. .......................................... 607/17
(58) Field of Classification Search ................. 607/4, 9, 607/17, 25
See application file for complete search history.

(56) References Cited

U.S. PATENT DOCUMENTS

| | | | |
|---|---|---|---|
| 3,057,356 A | 10/1962 | Greatbatch | |
| 3,253,596 A | 5/1966 | Keller | |
| 3,478,746 A | 11/1969 | Greatbatch | |
| 3,595,242 A | 7/1971 | Berkovits | |
| 3,648,707 A | 3/1972 | Greatbatch | |
| 3,747,604 A | 7/1973 | Berkovits | |
| 4,312,355 A | 1/1982 | Funke | |
| 4,386,610 A | 6/1983 | Leckrone | |
| 4,428,378 A | 1/1984 | Anderson et al. | |
| 4,432,362 A | 2/1984 | Leckrone et al. | |
| 4,476,868 A | 10/1984 | Thompson | |
| 4,523,593 A | 6/1985 | Rueter et al. | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,877 A | 3/1988 | Kallok | |
| 4,856,523 A | 8/1989 | Sholder et al. | |
| 4,856,524 A * | 8/1989 | Baker, Jr. ....................... | 607/17 |
| 4,880,005 A | 11/1989 | Pless et al. | |
| 4,890,617 A | 1/1990 | Markowitz et al. | |
| 4,932,046 A | 6/1990 | Katz et al. | |
| 4,941,471 A | 7/1990 | Mehra | |
| 4,953,551 A | 9/1990 | Mehra et al. | |
| 5,052,388 A | 10/1991 | Sivula et al. | |
| 5,085,215 A | 2/1992 | Nappholz et al. | |
| 5,097,832 A | 3/1992 | Buchanan | |
| 5,117,824 A | 6/1992 | Keimel et al. | |
| 5,133,350 A | 7/1992 | Duffin | |
| 5,144,950 A | 9/1992 | Stoop et al. | |
| 5,163,427 A | 11/1992 | Keimel | |
| 5,188,105 A | 2/1993 | Keimel | |
| 5,188,117 A | 2/1993 | Steinhaus et al. | |
| 5,228,438 A | 7/1993 | Buchanan | |

(Continued)

FOREIGN PATENT DOCUMENTS

EP   0363015   4/1990

(Continued)

*Primary Examiner* — Eric D. Bertram
(74) *Attorney, Agent, or Firm* — Stephen W. Bauer; Reed A. Duthler

(57) ABSTRACT

Rate responsive pacing is limited in an atrial based pacing mode by the AV interval in order to avoid or minimize ventricular encroachment of atrial pacing. The AV or VA interval is used to permit rate responsiveness; modulate rate responsiveness or to determine a dynamic upper sensor rate.

20 Claims, 7 Drawing Sheets

U.S. PATENT DOCUMENTS

| | | | |
|---|---|---|---|
| 5,273,035 | A | 12/1993 | Markowitz et al. |
| 5,292,340 | A | 3/1994 | Crosby et al. |
| 5,318,594 | A | 6/1994 | Limousin et al. |
| 5,334,220 | A | 8/1994 | Sholder et al. |
| 5,345,362 | A | 9/1994 | Winkler |
| 5,372,607 | A | 12/1994 | Stone et al. |
| 5,388,586 | A | 2/1995 | Lee et al. |
| 5,417,714 | A | 5/1995 | Levine et al. |
| 5,522,859 | A | 6/1996 | Stroebel et al. |
| 5,540,725 | A | 7/1996 | Bornzin et al. |
| 5,584,868 | A | 12/1996 | Salo et al. |
| 5,591,214 | A | 1/1997 | Lu |
| 5,626,623 | A | 5/1997 | Kieval et al. |
| 5,643,326 | A | 7/1997 | Weiner et al. |
| 5,674,257 | A | 10/1997 | Stroebel et al. |
| 5,697,958 | A | 12/1997 | Paul et al. |
| 5,725,561 | A | 3/1998 | Stroebel et al. |
| 5,741,308 | A | 4/1998 | Sholder et al. |
| 5,814,077 | A | 9/1998 | Sholder et al. |
| 5,836,974 | A | 11/1998 | Christini et al. |
| 5,861,007 | A | 1/1999 | Hess et al. |
| 5,873,895 | A | 2/1999 | Sholder et al. |
| 5,954,755 | A | 9/1999 | Casavant |
| 5,999,850 | A | 12/1999 | Dawson et al. |
| 6,058,326 | A | 5/2000 | Hess et al. |
| 6,122,546 | A | 9/2000 | Sholder et al. |
| 6,128,529 | A | 10/2000 | Esler et al. |
| 6,128,534 | A | 10/2000 | Park et al. |
| 6,141,586 | A | 10/2000 | Mower |
| 6,169,918 | B1 | 1/2001 | Haefner et al. |
| 6,198,968 | B1 | 3/2001 | Prutchi et al. |
| 6,256,541 | B1 | 7/2001 | Heil et al. |
| 6,321,115 | B1 | 11/2001 | Mouchawar et al. |
| 6,397,105 | B1 | 5/2002 | Bouhour et al. |
| 6,434,424 | B1 | 8/2002 | Igel et al. |
| 6,477,416 | B1 | 11/2002 | Florio et al. |
| 6,609,028 | B2 | 8/2003 | Struble |
| 6,654,637 | B2 | 11/2003 | Rouw et al. |
| 6,697,673 | B1 | 2/2004 | Lu |
| 6,731,980 | B1 | 5/2004 | Mouchawar et al. |
| 6,772,005 | B2 | 8/2004 | Casavant |
| 6,792,307 | B1 | 9/2004 | Levine et al. |
| 6,873,875 | B1 | 3/2005 | Gilkerson et al. |
| 6,904,315 | B2 | 6/2005 | Panken et al. |
| 6,925,326 | B1 | 8/2005 | Levine et al. |
| 6,978,175 | B1 | 12/2005 | Florio et al. |
| 7,027,868 | B2 | 4/2006 | Rueter et al. |
| 7,123,960 | B2 | 10/2006 | Ding et al. |
| 7,130,683 | B2 | 10/2006 | Casavant et al. |
| 7,218,965 | B2 | 5/2007 | Casavant et al. |
| 7,245,966 | B2 | 7/2007 | Betzold et al. |
| 7,248,924 | B2 | 7/2007 | Casavant |
| 7,254,441 | B2 | 8/2007 | Stroebel |
| 7,283,872 | B2 | 10/2007 | Boute et al. |
| 2002/0038482 | A1 | 4/2002 | Mennicke et al. |
| 2002/0041700 | A1 | 4/2002 | Therbaud |
| 2002/0082646 | A1 | 6/2002 | Casavant et al. |
| 2002/0128687 | A1 | 9/2002 | Baker et al. |
| 2002/0138417 | A1 | 9/2002 | Lawrence |
| 2003/0078627 | A1 | 4/2003 | Casavant et al. |
| 2004/0010292 | A1 | 1/2004 | Amblard et al. |
| 2004/0024694 | A1 | 2/2004 | Lawrence et al. |
| 2004/0078321 | A1 | 4/2004 | Lawrence |
| 2004/0117316 | A1 | 6/2004 | Gillum |
| 2004/0260349 | A1 | 12/2004 | Stroebel |
| 2005/0038482 | A1 | 2/2005 | Yonce et al. |
| 2005/0055059 | A1 | 3/2005 | Betzold et al. |
| 2005/0096708 | A1 | 5/2005 | Seim et al. |
| 2005/0177197 | A1 | 8/2005 | Betzold |
| 2005/0267539 | A1 | 12/2005 | Betzold et al. |
| 2005/0273430 | A1 | 12/2005 | Pliha |
| 2007/0203523 | A1 | 8/2007 | Betzold |
| 2007/0213777 | A1 | 9/2007 | Betzold et al. |

FOREIGN PATENT DOCUMENTS

| | | |
|---|---|---|
| EP | 0448193 | 9/1991 |
| EP | 0624386 | 11/1994 |
| EP | 0830877 | 3/1998 |
| EP | 1449562 | 8/2004 |
| WO | WO 02/051499 | 0/2002 |
| WO | WO 95/32758 | 12/1995 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |

* cited by examiner

SELF LIMITED RATE RESPONSE

CROSS REFERENCE TO RELATED APPLICATION

This application is a continuation application of Ser. No. 10/971,686, now issued as U.S. Pat. No. 7,248,924, filed Oct. 25, 2004 entitled, "Self Limited Rate Response," which was invented by Casavant et al.

FIELD OF THE INVENTION

The present invention relates to implantable medical devices and mores specifically to implantable medical devices having rate response capabilities.

BACKGROUND OF THE INVENTION

While a variety of pacing modes are available, dual chamber pacing/sensing (DDD) is commonly utilized. With a DDD mode, atrial and ventricular events are both sensed. If an expected intrinsic event is not sensed within a predetermined time window, an appropriate atrial or ventricular pacing stimulus is delivered. This mode provides a great deal of control over the patient's cardiac rhythm and the timing (e.g., the atrial-ventricular or AV delay) may be modified based upon many different factors. One of the many benefits provided by the DDD mode is the ability to maintain AV synchrony. That is, for any given atrial event there will be a specifically timed ventricular event, either intrinsic or paced.

Another beneficial feature is rate response (RR) pacing. With rate responsive pacing, a demand sensor is provided that seeks to approximate activity levels or physiological need from the patient and increase or decrease the pacing rate accordingly. For example, an accelerometer is used to sense the patient's motion. As the patient is more active, the accelerometer senses increased movement. This is recognized by the implantable medical device (IMD), which could be, for example, an implantable pulse generator (IPG) or implantable cardioverter defibrillator (ICD) with pacing capabilities. In any event, the accelerometer's signal causes the IMD to pace at a higher rate. The assumption is that increased patient activity requires higher cardiac output and increasing the patient's heart rate (i.e., pacing rate) will lead to greater cardiac output. The higher the activity levels sensed, the higher the paced rate, up to a predetermined maximum rate. There are a variety of demand sensors the may be employed such as, a minute ventilation sensor, blood oxygen sensor, chemical sensors, motion/movement sensors, or any other device that will approximate one or more demand parameters of the patient.

Typically, rate responsiveness is a positive feature that allows patients to engage in higher activity levels than would be possible with fixed rate pacing. The combination of DDD with rate response is also generally positive in that as the pacing rate is increased, the DDD mode will adjust parameters to assure proper timing throughout the cardiac cycle.

Recently, there has been a recognition that conducted or intrinsic ventricular depolarizations are vastly preferable to ventricular pacing in general and pacing in the right ventricular apex in particular. The difficulty in facilitating this preference is that in a great many patients, the intrinsic AV delay is so long that DDD timing will almost always deliver a ventricular pace. In order to minimize or greatly reduce ventricular pacing, a protocol had been provided that, in one embodiment, utilizes an atrial based timing mode that allows a full cardiac cycle to elapse without ventricular activity; thus providing the greatest opportunity to safely allow intrinsic conduction whenever possible. These protocols are described in U.S. Ser. No. 10/755,454, filed Jan. 12, 2004, entitled "Preferred ADI/R: A Permanent Pacing Mode to Eliminate Ventricular Pacing While Maintaining Backup Support", which is a continuation of U.S. Ser. No. 10/246,816, filed Sep. 17, 2002, entitled "Preferred ADI/R: A Permanent Pacing Mode to Eliminate Ventricular Pacing While Maintaining Backup Support", which is a continuation-in-part of U.S. Ser. No. 09/746,571, filed Dec. 21, 2000, entitled "Preferred ADI/R: A Permanent Pacing Mode to Eliminate Ventricular Pacing While Maintaining Backup Support", recently granted as U.S. Pat. No. 6,772,005 which are herein incorporated by reference in their entireties.

As used herein, an atrial based pacing mode is a mode that is programmed to pace in the atria, but only to sense in the ventricles. True single chamber atrial pacing would imply that only a single lead is present and ventricular activity may not be sensed in the ventricle nor would ventricular pacing be deliverable. In the present context we discuss an IMD operating in an atrial based mode, but at least having ventricular sensing capabilities. Though not required, such a device would generally include ventricular pacing. However, in order to deliver ventricular pacing the device would typically mode switch to a different mode, such as DDD.

Atrial based pacing in general, as well as in the context of minimizing ventricular pacing as discussed above, may also include a rate response function. Once again, as the demand sensor indicates a greater need, the heart rate is elevated by increasing the atrial pacing rate. However, without ventricular pacing, there is no control over the ventricular timing. As such, if the AV delay is not shortened or is actually elongated by the AV node in response to the elevated pacing rate, overall timing may become skewed. That is, the A-A interval is decreasing with respect to the resting rate, but the AV delay is not correspondingly and correctly modified. As a consequence, the VA delay (ventricular to atrial delay) may be shortened. Another consequence may be Wenckebach block. Thus, given ratios of ventricular beats are not conducted with respect to the atrial rate. As such, even though the atrial rate may rise, the effective ventricular rate could actually decrease.

If the VA delay becomes too short over a prolonged period of time, negative consequences may result. The contraction of the ventricles takes a finite amount of time from initiation of a depolarization. If the contraction is not completed, a subsequent atrial contraction will attempt to force blood into a contracted ventricle. Often, this results in blood flow out of the atria and back towards the lungs or venous system, causing symptoms. Similarly, the ventricles even if not fully contracted may not be fully relaxed during the atrial contraction, resulting in diminished filling. The net effect of having inadequate VA delay is that the elevation in heart rate fails to increase cardiac output, may actually reduce cardiac output, may affect hemodynamic compromise, and/or cause patient symptoms.

DETAILED DESCRIPTION

Figure 1:
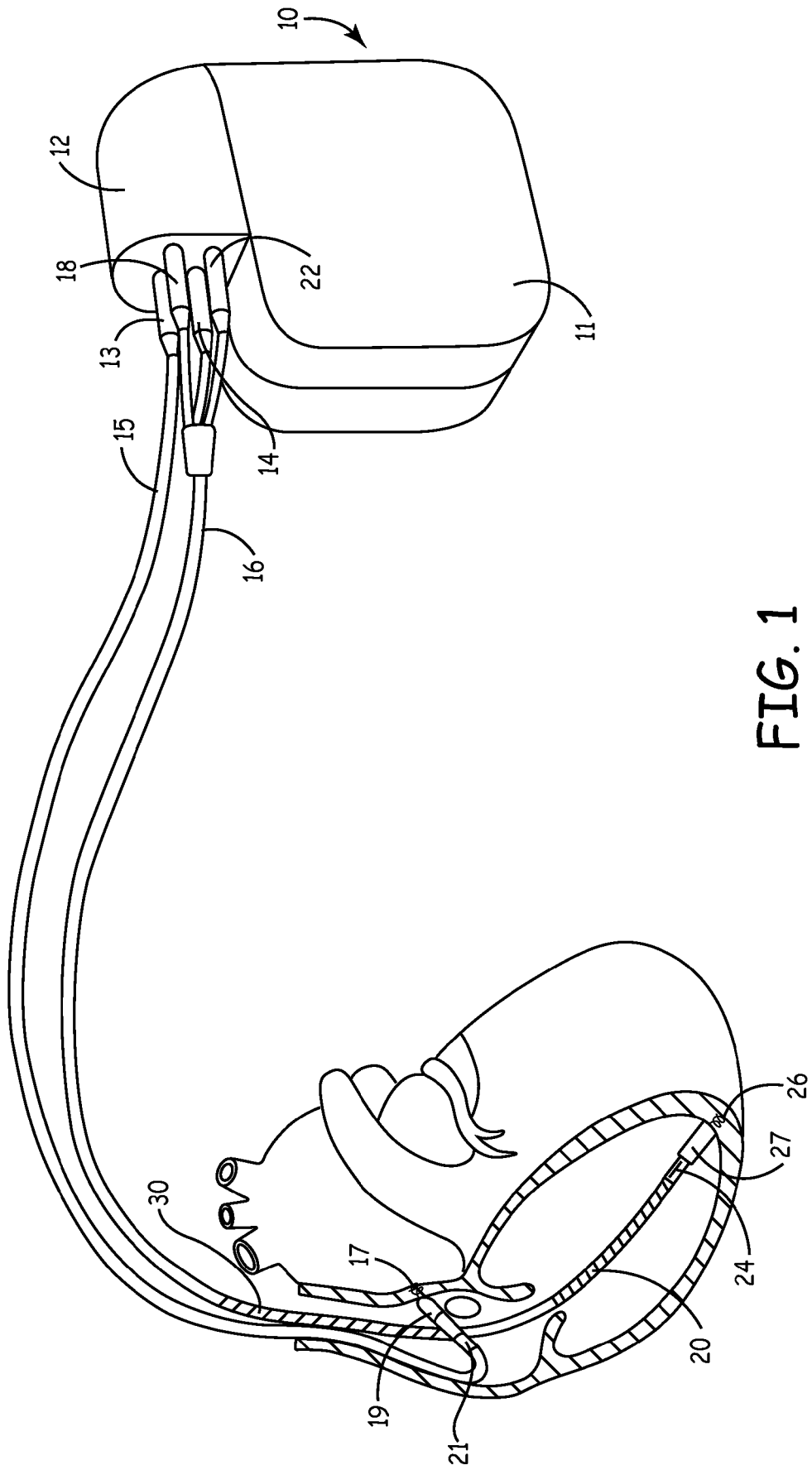
FIG. 1 is an illustration of an ICD system according to the present invention.

Referring now to FIG. 1, there are illustrated an ICD 10 and leads 15 and 16, making up the system. ICD 10 is an implantable cardioverter defibrillator. It should be appreciated that such a device may include pacing, defibrillation, cardioversion, and/or other therapies alone or in any combination. The leads shown are illustrative, it being noted that other specific forms of leads are within the scope of this invention. Ventricular lead 16 as illustrated has, located adjacent to the distal end, an extendable helix electrode 26 and a ring electrode 24, the helix electrode being mounted retractably within an insulative head 27. Electrodes 24 and 26 are used for bipolar ventricular pacing and for bipolar sensing of ventricular depolarizations. While electrodes 24 and 26 may be used for bipolar pacing and sensing, electrode 26 may be used in conjunction with the surface of device casing 10, which surface acts as a common or indifferent electrode in what is termed unipolar operation. Ventricular lead 16 also carries a coil electrode 20, sometimes referred to as the RV (right ventricular) coil, for delivering defibrillation and/or cardioversion pulses. Coil electrode 20 is positioned on lead 16 so that when the distal tip is at the apex of the ventricle, coil 20 is positioned in the right ventricle. Lead 16 may also carry, optionally, an SVC coil 30, which can be used for applying cardioversion pulses. Lead 16 carries respective concentric coil conductors (not shown), separated from one another by appropriate means such as tubular insulative sheaths and running the length of the lead for making electrical connection between the ICD device 10 and respective ones of electrodes 20, 24, 26 and 30.

Atrial lead 15 as illustrated includes an extendable helix electrode 17 and a ring electrode 21, the helix electrode being mounted retractably within an insulative head 19. Electrodes 17 and 21 are used for bipolar atrial pacing and for sensing atrial depolarizations. While electrodes 17 and 21 may be used for bipolar pacing and sensing, electrode 17 may be used in conjunction with the surface of device casing 10, which surface acts as a common or indifferent electrode in what is termed unipolar operation. Note that, in this example, atrial lead 15 is not equipped with coils for use in the sensing and delivery of cardioversion of defibrillation pulses. This is not meant to preclude the inclusion of such applications that may be used advantageously with the present invention.

As indicated, the present invention may be used in an atrial based pacing mode, where ventricular pacing is selectively precluded, though a ventricular lead is present. The ventricular lead will provide sensing capabilities and when appropriate, pacing or other therapies. It should be appreciated that the present invention is also applicable to true atrial based devices that is when no ventricular lead is provided; ventricular sensing is accomplished in such a case through far-field sensing of the R-wave in the atrial channel.

An ICD device 10, is shown in combination with atrial and ventricular leads, with the lead connector assembly 13,14, 18, and 22 being inserted into the connector block 12 of the device 10. A specific example of a defibrillation pulse generator that may be used in conjunction with the present ventricular lead is disclosed in U.S. Pat. No. 4,953,551. Other ICD type units can be used; reference is made to U.S. Pat. Nos. 5,163,427 and 5,188,105 as disclosing illustrative forms of apparatus for delivering cardioversion and defibrillation pulses. As used herein, the term "ICD type" device refers to any device that can apply both pacing therapy and shock therapy for controlling arrhythmias.

Figure 2:
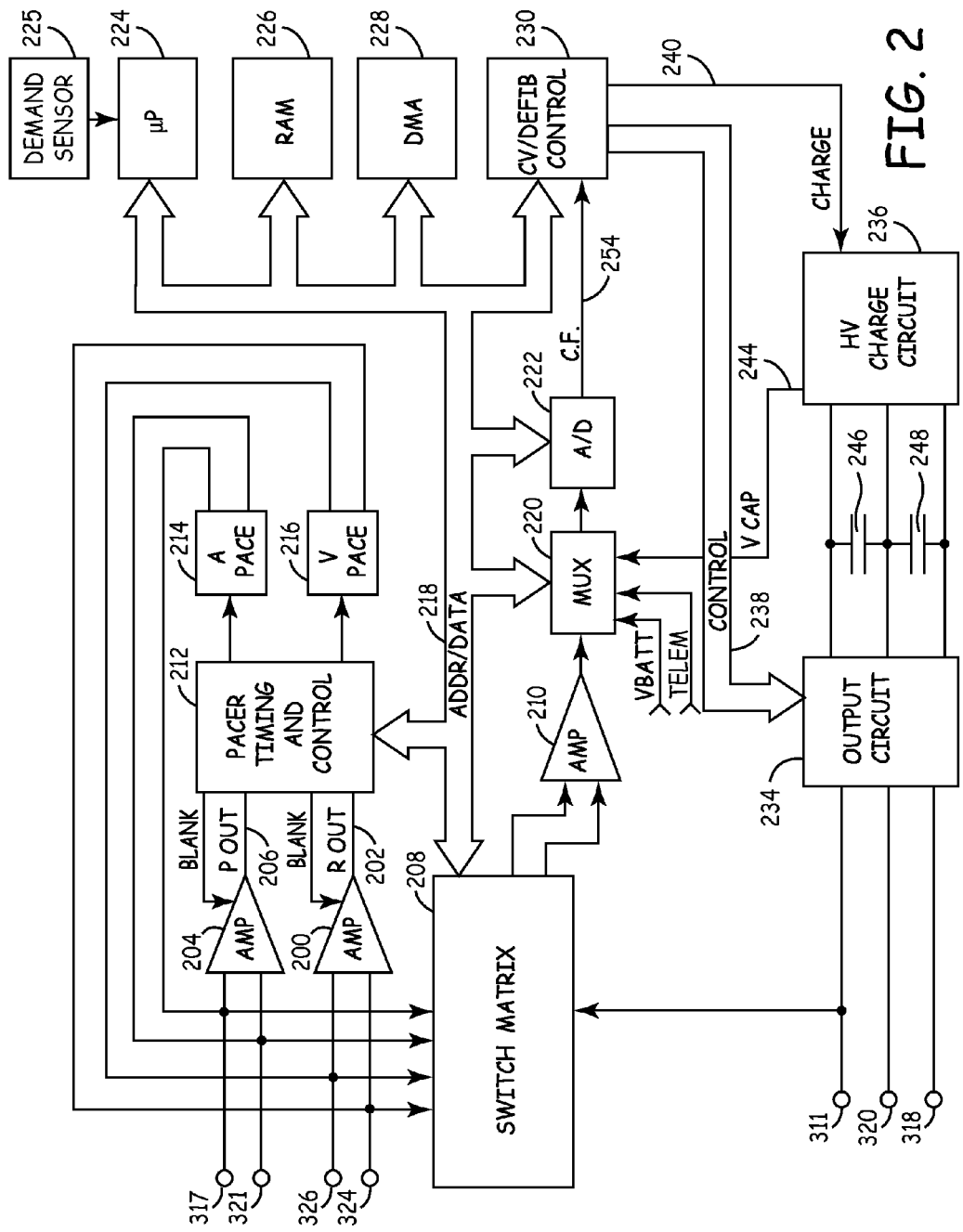
FIG. 2 is a block, functional diagram of ICD adapted to carry out the features of the present invention.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 16, and is the uninsulated portion of the housing of the ICD 10. Electrode 320 corresponds to electrode 20 and is a defibrillation electrode located in the right ventricle. Electrode 318 corresponds to electrode 30 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5-200 Hz) amplifier 210 for use in signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves will not restart the escape pacing interval timing. The durations of these intervals are determined by microprocessor 224, in response to stored data in memory 226 and are communicated to the pacing circuitry 212 via address/data bus 218. Pacer circuitry 212 also determines the amplitudes and pulse widths of the cardiac pacing pulses under control of microprocessor 224. A demand sensor 225 is communicatively coupled with the microprocessor 224 and provides and signal indicative of a physical parameter. For example, the demand sensor 225 may be an accelerometer used to sense motion of the patient's body. Demand sensor 225 may be a minute ventilation sensor, blood oxygen sensor, combination of sensors, or any type of sensor that provides an indication of the patient's cardiac demand. Demand sensor data is passed to the pacing control circuitry 212. Alternatively, the demand sensor 225 is directly coupled with the pacing control circuitry 212.

During pacing, the escape interval timers within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval timers are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval timers when reset by sensed R-waves and P-waves may be used to measure the durations of R-R intervals, P-P intervals, P-R intervals, and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the ICD may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, might also be usefully employed in alternative embodiments of the ICD.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval timers therein and to define refractory periods during which detection of R-waves and P-waves is ineffective to restart the escape interval timers. Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval timer to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

Figure 3:
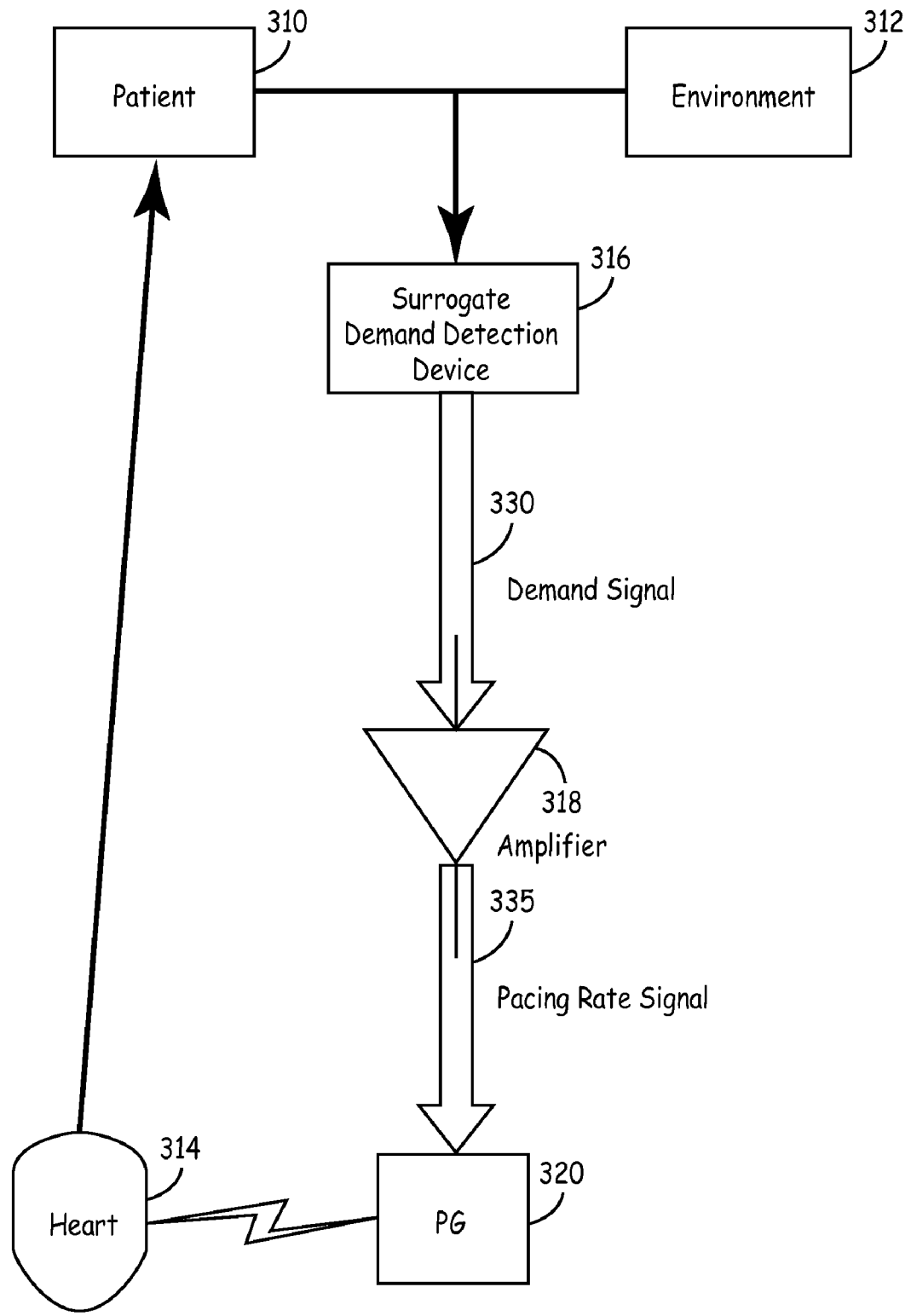
FIG. 3 is a schematic diagram of a rate response system.

FIG. 3 schematically illustrates conventional rate responsive pacing. A surrogate demand detection device 316 senses physical parameters from the patient 310 and/or the environment 312. Demand detection device 316 may be, for example, the demand sensor 225. Patient parameters may include movement, activity levels, chemical levels, blood gas saturation levels ($O_2$, $CO_2$) or the like. Environmental parameters are meant to indicate external factors perceived to require an increased demand. For example, slow movement down a flight of stairs may produce jarring recognized by an accelerometer as a need for increased demand, when the body does not actually require increased demand.

Based on the physical parameters, the demand detection device outputs a demand signal 330 that is processed by an amplifier 318. The amplified demand signal 330 is output as a pacing rate signal 335 to the pulse generator 320, under control of the pacing circuitry 212. The pacing rate signal 335 causes the pulse generator to pace the heart 314 at an elevated rate, with the rate correlated to the demand perceived by the detection device 316. The resultant elevated rate of the heart 314 affects the patient 310. When the perceived demand diminishes, the demand signal 330 is correspondingly diminished and the pacing rate is gradually lowered.

Thus, within programmed limits an increase in perceived demand by the detection device 316 leads to an elevated pacing rate. When the perceived demand is present, the ICD 10 attempts to satisfy this demand by increasing the pacing rate. With a higher rate, cardiac output is assumed to increase and thus, satisfy the demand. While operating in a DDD mode, the complete cardiac cycle is managed and the increased pacing rate is accommodated. Thus, a higher pacing rate generally results in increased cardiac output.

In an atrial based pacing mode, where ventricular pacing is generally not provided, an elevated pacing rate might not lead to higher cardiac output. Cardiac output is the measure of blood pumped for a given period of time. The components of cardiac output include heart rate and stroke volume. These two components are not necessarily independent of one another and stroke volume is not as dynamically variable as heart rate. An increase in rate often reduces the stroke volume because of reduced filling times. Wenckebach block may also occur, thereby reducing the effective ventricular rate despite an increase in the atrial rate. In addition, the heart requires more energy at the higher rate, thus increasing its own demand for oxygenated blood. Therefore, in order for an elevated pacing rate to increase cardiac output, the increase gained from the rate component must offset the reduction in stroke volume and higher physiological demands that result.

In response to an elevated heart rate (paced or intrinsic), the AV node should normally adjust the AV delay to ensure proper timing. In some patients, this does not occur and the AV delay becomes excessively long with respect to the rate. This might result from a deficiency in the autonomic response mechanism, the AV node, or along the conduction pathway. Furthermore, since a foreign sensor perceives the demand, the autonomic response, even if functional, might not affect the AV node with sufficient speed.

As the AV delay increases, the VA delay correspondingly decreases, assuming a fixed A-A interval dictated by a pacing rate. When the VA becomes too short (VA encroachment) for a prolonged period of time, negative effects may result. As previously discussed, the ventricles may be fully contracted when the subsequent atrial contraction occurs. Alternatively, the ventricles may be only partially relaxed during that subsequent atrial contraction. The result is that stroke volume is moderately to severely reduced and/or Wenckebach block. When this occurs, the elevated pacing rate does not actually increase cardiac output and may in fact reduce it. At the very least, elevated pacing is not beneficial and potentially may be counterproductive in these instances. For example, retrograde conduction may occur.

The present invention provides for a rate response feedback such that a pacing rate is not simply dictated by a given demand sensor output or rate response logic. Rather, the VA interval is monitored and if the VA interval falls within a predetermined range, the demand signal is either modulated to reduce the pacing rate or is effectively ignored, thus maintaining pacing at a resting rate.

Figure 4:
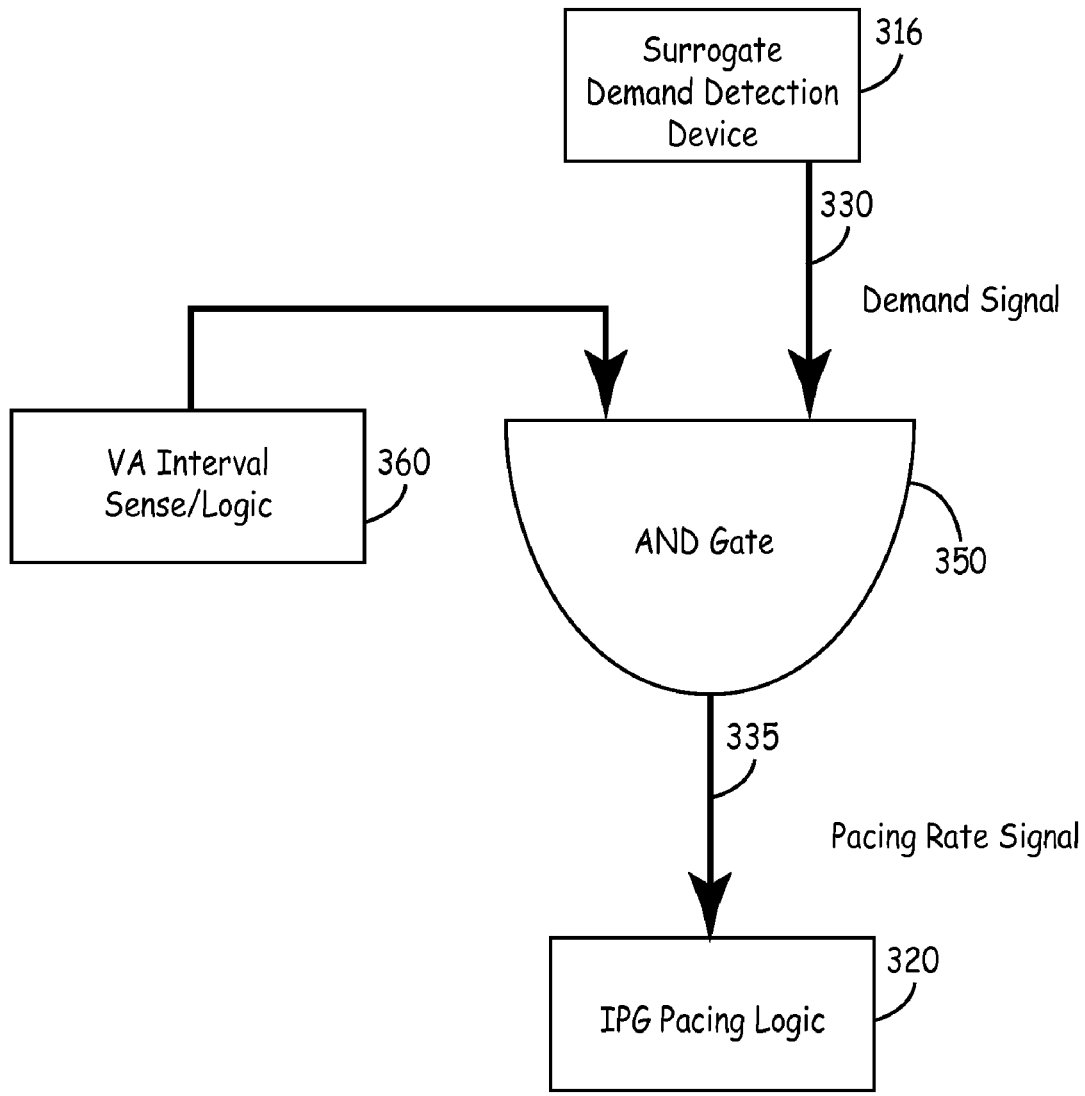
FIG. 4 is a schematic diagram of a closed loop rate response system incorporating VA interval central.

FIG. 4 schematically illustrates a logical arrangement of one embodiment of the present invention. In this embodiment, the VA interval is monitored by VA interval logic 360, which may be a separate component but would typically be a capability of the pacing circuitry 212. The outputs of the VA interval logic 360 and the demand sensor 316 are directed to a gate 350. The output of the gate 335 becomes the pacing rate signal 335 and is provided to the pacing logic 320. In summary, the gate 350 will only pass the demand signal 330 if the VA interval logic 360 indicates that the measured VA intervals are within acceptable parameters. If not, the demand signal 330 does not pass and the pacing logic 320 paces at the resting rate.

In practice, gates may be used to permit or limit the actual demand signal or logic gates may be utilized to cause the demand signal 330 to be ignored or utilized. For example, gate 350 could be an AND gate. If the demand sensor 316 outputs a demand signal to increase pacing, it may also output a logical high into the gate 350. Similarly, if the VA interval is within acceptable parameters, then the output to the gate 350 is high. Thus, the output of the AND gate is high, and the pacing logic will then utilize the demand signal 330. If the VA interval is too short, then the output of the VA interval logic is low and thus the AND gate output is low. The demand signal 330 is not considered. Of course, any logical arrangement achieving such a result may be employed. This embodiment effectively precludes the demand sensor 316 from increasing the pacing rate if the VA interval is too short.

The parameters for determining whether the VA interval is too short may be selected based upon either generalized or patient specific parameters. In one embodiment, VA intervals less than 350 ms are deemed too short. In another embodiment, a VA interval of less than 200 ms is deemed to short. In another embodiment, a VA interval of less than 100 ms is deemed to short while in another embodiment, VA intervals of less than 50 ms are deemed too short. Furthermore, the determinations may be made on a beat-to-beat analysis or based on averaged value over a predetermined number of cardiac cycles. In addition, the measured intervals for the averaged values may be analyzed to exclude anomalous intervals or cardiac events.

If the measured VA interval is too short, the demand signal is precluded from increasing pacing and/or the pacing rate will actually be reduced, e.g., to a resting rate by a predetermined amount or to another rate. As time progresses, the autonomic response may affect the heart and cause the AV node to decrease the AV delay. If this occurs and the demand sensor 316 still indicates a need, the pacing rate may be elevated at that time. Of course, a more complex algorithm may be established. For example, the VA interval may be required to be below the threshold for a predetermined period of time or predetermined number of cycles prior to excluding the demand signal.

Figure 5:
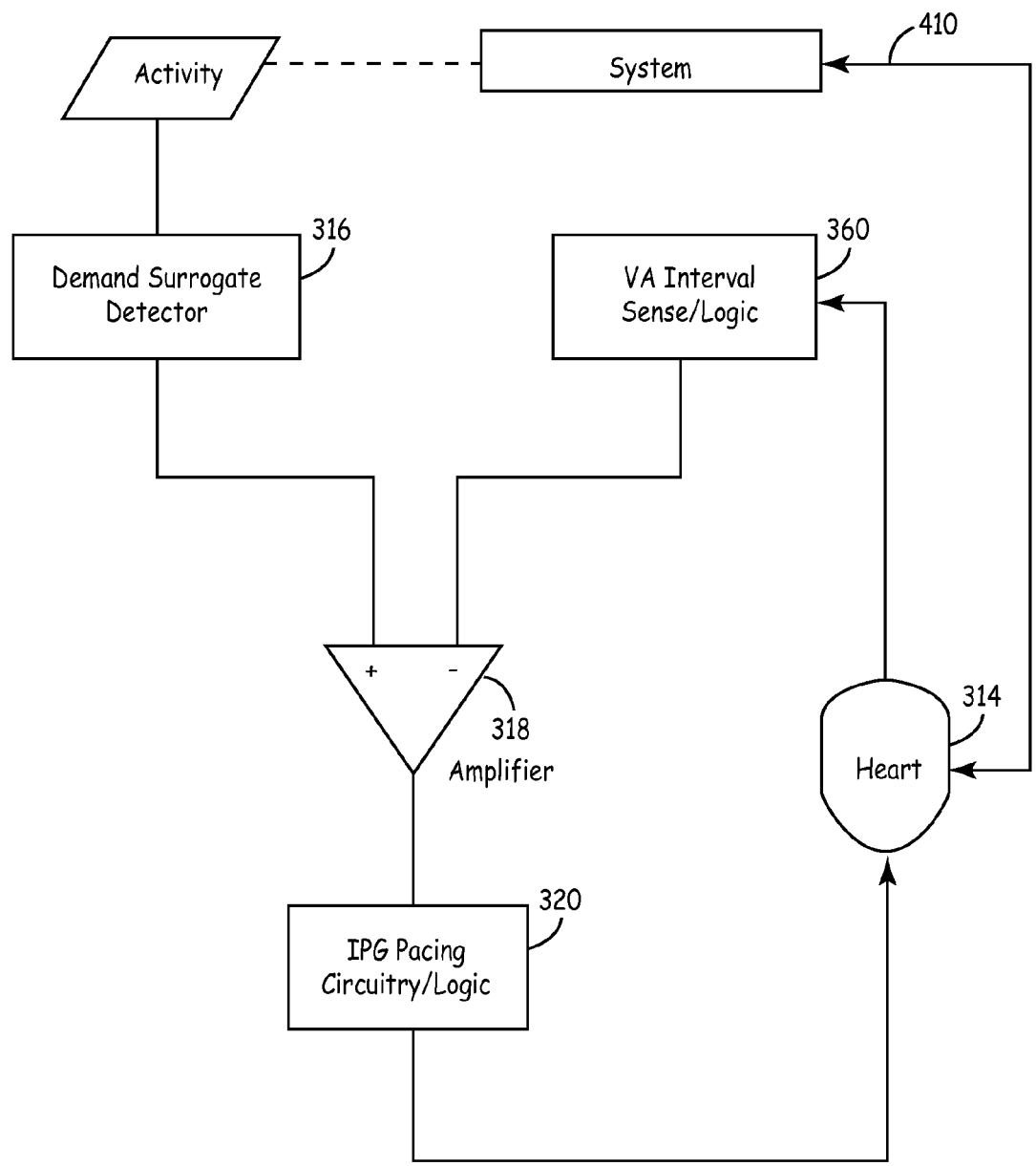
FIG. 5 is a schematic diagram of a closed loop rate response system incorporating VA interval central.

FIG. 5 schematically illustrates another embodiment of the present invention. In this embodiment, the measured VA interval will have one of three effects with respect to rate responsiveness. If the VA interval is acceptable, the demand sensor output will cause an elevation in the pacing rate. If the VA interval is too short, the demand sensor output will be ignored and the pacing rate will remain at (or return to) the lower rate (or to an acceptably low rate). Finally, if the VA interval falls within an intermediate range, the demand signal is modulated to produce an appropriate pacing rate.

Figure 6:
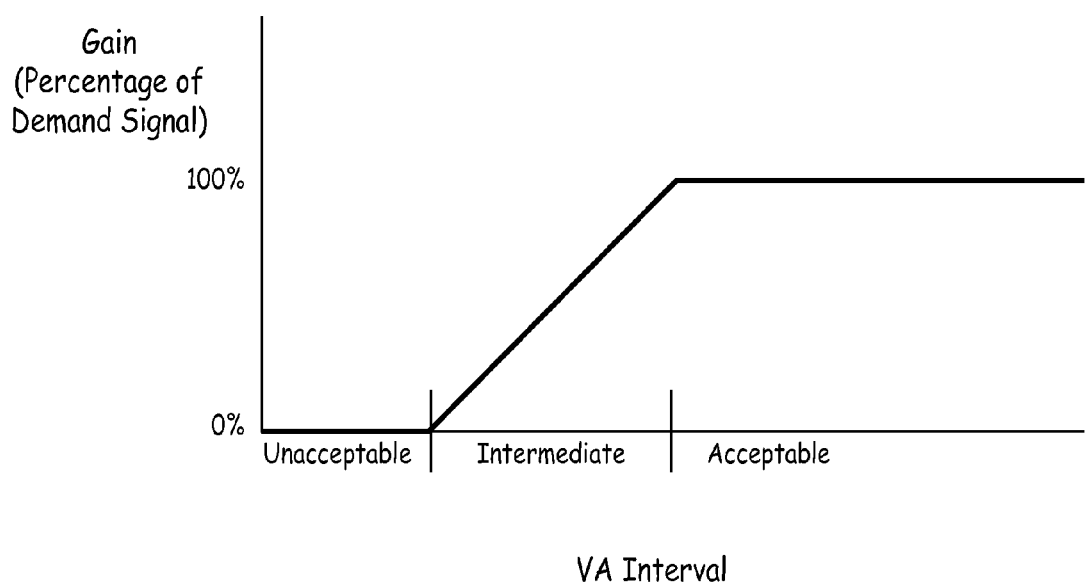
FIG. 6 is a graph illustrating gain provided by VA interval ranges.

In one embodiment, the VA interval logic 360 will effectively act as a gain adjustment of the output of the demand detector 316. FIG. 6 illustrates a graph of the gain resulting from the measured VA interval. While the measured VA interval is too short, or within the unacceptable range, the gain is 0 and the demand signal is effectively ignored or blocked. When the VA interval is sufficiently long and falls within the acceptable range, the gain is 100% and the full demand signal is utilized to determine the pacing rate. When the measured VA interval falls within the intermediate range, the gain value is set between 0% and 100%. As illustrated, the modulation may be linear and directly correlated to the measured VA interval. Alternatively, any linear slope or non-linear curve may be employed. In other embodiments, the intermediate gain may be set to a fixed rate, e.g., 50% for any value falling within the intermediate range. A stepped gain may be provided within the intermediate VA interval range. That is, the intermediate range may be further subdivided, and a single gain value may be provided for each subdivision (e.g., 25%, 50%, and 75%).

The VA interval values selected to define the unacceptable, intermediate, and acceptable ranges may be set generally or with patient specific information. For example, patients may be paced in a controlled environment with varying VA intervals and monitored for effect. The results would then be utilized to set the specific range values for that patient. In one embodiment, VA delays of between 0 to approximately 100 ms would be considered unacceptable; 100 ms to 200 ms would be considered intermediate; and greater than approximately 200 ms would be acceptable.

Returning to FIG. 5, the appropriate parameters 400 are sensed by the demand sensor 316. The output from the demand sensor is applied to the amplifier 318 and the amplifier 318 outputs a demand signal to the IPG pacing circuitry/logic 320. If otherwise unmodified, this signal will cause the pacing rate to increase up to the predefined maximum in direct correlation to the output of the demand detector 316. The pacing circuitry/logic 320 paces the heart 314 as needed, at the selected rate.

The activity of the heart 314 is monitored by the VA interval sense logic 360 and, in particular, the VA intervals are measured or calculated. Assuming the VA interval falls within the acceptable range (e.g., FIG. 6), the VA interval logic 360 will not affect the output of the demand detector 316. If the VA intervals are in the unacceptable range, then the VA interval sense logic 360 will cancel or preclude the signal from the demand detector 316. This may be accomplished in a variety of ways. For example, the absolute value output from the VA interval sense/logic 360 to the amplifier 318 may be proportionally equal (or even greater) than the absolute value of output from the demand sensor. The VA interval sense/logic output is provided to a negative input of the amplifier 318 whereas the demand output is provided to a positive input. Thus, if the VA interval sense/logic output is equal to or greater in magnitude than the demand output, the amplifier output will be zero or negative. A negative value will serve to decrease the pacing rate if already elevated.

If the VA interval of the heart 314 is within the intermediate range, the value of the VA interval sense/logic output is proportionally modulated. That is, the demand sensor output will be permitted to affect the pacing rate, but in a reduced manner. Thus, the VA interval sense/logic output will have an absolute value that is smaller than that of the demand sensor output resulting in a lowered demand output from the amplifier 318.

In order to provide the appropriate values, the demand detector 316 and the VA interval sense/logic log 360 are in communication. In another embodiment, the appropriate values are predetermined and preprogrammed. Alternatively, any other type of logic or control mechanism may be employed to preclude an increase and/or require a reduction in rate responsive pacing if the VA interval is in the unacceptable range. For example, switching may be employed to either permit or inhibit rate responsiveness when the VA interval is within the acceptable or unacceptable range. While in the intermediate range, the proportional adjustment may be made with hardware (e.g., logic), firmware, software or the like.

As illustrated in FIG. 5, the patient's autonomic nervous system 410, if functional or at least partially functional, will affect and is affected by the heart 314. Ideally, the autonomic nervous system (ANS) 410 will respond to the same physical conditions and physiological requirements that are being sensed (or at least a surrogate thereof) by the demand sensor 316. Thus, a dotted line illustrates a connection between the sensed activity 400 and ANS 410. The line is dotted, rather than solid to indicate two concepts. The first is that because the demand sensor 316 senses surrogate conditions (e.g., accelerometer output), the "sensed" demand may not actually result from physiological need. The second is that when there is in fact physiological need, the ANS 410 may be delayed, ineffective or otherwise sub-optimal in certain patients.

Such deficiency may manifest itself in a number of ways. Initially, the ANS 410 may fail to increase the intrinsic pacing rate of the heart 314. This, of course, is one reason why a demand sensor 316 is beneficial to begin with. Additionally, when the heart rate is elevated through pacing, the ANS 410 should respond and affect the AV node. The proper response would be to decrease the AV delay. Thus, physiological problems with the ANS 410 and/or the AV node may preclude modification of the AV delay, delay modification, or extend the period of adjustment.

As such, the VA interval sense/logic 360 may reduce or preclude an elevated pacing rate for a period of time. Then, assuming the demand still exists, the ANS 410 and/or the AV node may eventually shorten the AV delay. When this occurs, the VA interval will become longer and this is sensed. If the VA interval length reaches the acceptable or intermediate range, then an elevated rate or higher elevated rate is permitted.

Figure 7:
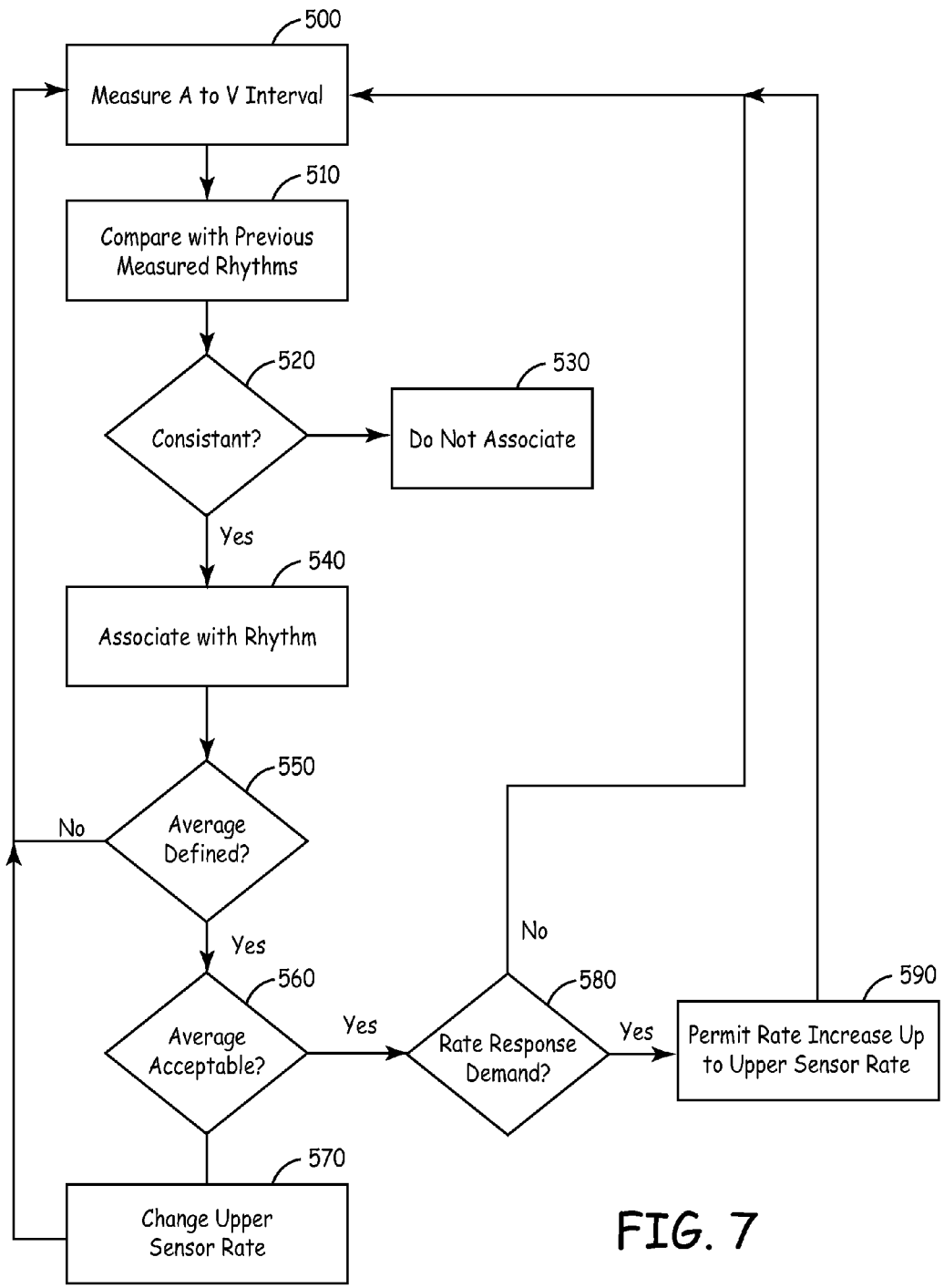
FIG. 7 is a flowchart illustrating a process for modulating rate responsiveness based upon upper sensors rates and encroachment.

FIG. 7 is a flowchart illustrating another process for addressing VA encroachment. While atrial based pacing is in effect, the AV interval is monitored (500). That is, the atrial event is generally paced and the ventricular event is intrinsic and thus, the AV duration is not directly controllable in this mode. Similarly, while the A-A interval is controllable by the device, the VA interval is uncontrolled because of the intrinsic nature of the ventricular event.

As previously discussed, sporadic VA encroachment is usually non-problematic and any negative effects that would occur typically result if the pattern is present for a longer period of time. Thus, the present embodiment utilizes averaged values rather than reacting to individual cardiac cycles. The measured AV interval is compared (510) with a predetermined number of previous measurements. A determination is made as to whether the current rhythm is consistent (520) with these previous cycles. If not, the current rhythm is not associated (530) with the averaged rhythm. Conversely, if the current rhythm is consistent with the averaged rhythm it is associated (540).

Generally, this process is provided to define an averaged or patterned AV timing, rather than proceeding based upon individual cardiac cycles. For example, the eight most recent cardiac cycles are evaluated and the AV intervals compared. If six of these AV intervals vary from one another by less than some variable, e.g., 40 ms, or by some predetermined percentage, then an associated rhythm is defined. The number of cycles considered, the variable offset and the number of consistent required to define an associated pattern may be selected as desired. Of course, the AV intervals from some fixed, predetermined number of cycles may simply be averaged together to define a pattern; however, this result may be somewhat skewed during transitional periods such as initiating higher activity levels or by unusual, individual cycles or cardiac events.

In any event, an average AV duration for some relevant time frame is defined (550). A useable average might not be defined until the appropriate number of consistent cardiac cycles occurs; if so, the process returns to (500) to continue to collect data or the average is based on the available data set.

The averaged AV interval is then evaluated to determine if it is acceptable (560). An acceptable averaged AV interval will depend upon the A-A pacing interval. For example, the A-A interval should be longer than the AV interval by at least some predetermined nominal value. In one embodiment, this nominal value is 150 ms. Thus, the VA interval will be at least 150 ms. In other embodiments, the nominal value is selected from a range between 50 ms to 350 ms, and in other embodiments is 50 ms, 100 ms, 200 ms, 250 ms, or 300 ms. If the averaged AV interval is acceptable, then rate response is considered (580) or allowable. An increase in the pacing rate is permitted (590) up to the upper sensor rate limit, which is now defined based in part upon the averaged AV interval. In other words, rate response is only permitted if the desired A-A interval will exceed the VA interval by the predetermined nominal value. Subsequently, the process returns to (500) and continues to monitor AV intervals.

If the averaged AV interval is unacceptable (560), the upper sensor rate limit is modified. Obviously, if there is a concurrent increase requested by the rate response algorithm, it will be declined. In addition, the pacing rate may be reduced to a level where the A-A interval exceeds the AV interval by the predetermined nominal value. This becomes the upper rate limit (570). Subsequently, the process returns to (500) and continues to monitor AV intervals.

Thus, the present embodiment averages AV intervals over a number of cardiac cycles and dynamically adjusts an upper rate limit to preclude VA encroachment. This can be used to initially establish an upper rate limit for a given patient and or to continually modify the upper rate limit. Furthermore, any appropriate rate response is permitted up to the dynamic upper rate limit.

As the averaged AV interval may vary depending upon the current A-A interval, the process continually or routinely monitors the AV delay and adjust the upper rate limit accordingly. If, over time, the intrinsic AV delay changes, the new data will automatically be incorporated into a new dynamic upper rate limit. However, there may be situations where the intrinsic AV delay will not improve or vary until higher rates are achieved. Thus, the upper rate limit may be periodically exceeded by the device, based upon demand, to verify the validity of the dynamic upper rate limit. For example, at a moderately elevated heart rate, the intrinsic AV delay may be inadequate and thus the upper rate limit is set at a lower value; however, if the pacing rate is further elevated, the intrinsic AV delay may self correct or otherwise improve at this higher rate. Thus, with a rate response request for increased demand that is being limited by the dynamic upper rate limit, this limit may be periodically exceeded over a sufficient number of cardiac cycles to determine averaged values. Then, the upper rate limit may be increased to accommodate the demand, if appropriate, or maintained at its previous value.

As used throughout, various timing intervals are measured, monitored, or calculated. It should be appreciated that many of these intervals are related and that the use of one such interval in a given embodiment is not meant to exclude or preclude the others. For example, the A-A interval includes the AV interval and the VA interval. Any two may be used to determine the other.

Although the present invention has been described with reference to preferred embodiments, persons skilled in the art will recognize that changes may be made in form and detail without departing from the spirit and scope of the invention.

The invention claimed is:

1. A method comprising:
measuring an AV interval;
determining an averaged AV interval over a predetermined number of cardiac cycles; and
setting a minimum A-A interval equal to the averaged AV interval plus a predetermined constant; and
delivering cardiac pacing in a rate responsive, atrial based pacing mode; comprising:
sensing a physiologic parameter other than the AV interval;
determining an atrial pacing rate based upon the sensed physiological parameter; and
employing the set minimum A-A interval as an upper limit to the determined atrial pacing rate.

2. The method of claim 1, wherein the predetermined constant is 150 ms.

3. The method of claim 1, further comprising:
analyzing the measured AV interval;
determining if the measured AV interval is associated with a pattern; and
excluding the measured AV interval from the averaged AV interval unless the measured AV interval is associated with the pattern.

4. The method of claim 1, wherein the predetermined constant is selected from a range between 50 ms and 350 ms.

5. The method of claim 1, wherein the sensed physiological parameter comprises minute ventilation.

6. The method of claim 1, wherein the sensed physiological parameter comprises blood oxygen.

7. The method of claim 1, wherein the sensed physiological parameter comprises movement.

8. The method of claim 1, wherein the sensed physiological parameter comprises activity.

9. The method of claim 1, wherein the sensed physiological parameter comprises a chemical level.

10. The method of claim 1, wherein the sensed physiological parameter comprises a blood gas saturation level.

11. The method of claim 1, wherein the sensed physiological parameter comprises a combination of sensors.

12. The method of claim 1, wherein the sensed physiological parameter comprises an indication of cardiac demand.

13. A method comprising:
measuring an AV interval;
determining an averaged AV interval over a predetermined number of cardiac cycles;
setting a minimum A-A interval equal to the averaged AV interval plus a predetermined constant;
delivering cardiac pacing in a rate responsive, atrial based pacing mode employing the set minimum A-A interval as an upper rate limit;
analyzing the measured AV interval;
determining if the measured AV interval is associated with a pattern; and
excluding the measured AV interval from the averaged AV interval unless the measured AV interval is associated with the pattern
wherein the measured AV interval is associated with the pattern if a duration of the measured AV interval varies by less than a predetermined amount from previously measured subset of AV intervals.

14. The method of claim 13, wherein the predetermined constant is selected from a range between 50 ms and 350 ms.

15. The method of claim 13, wherein delivering cardiac pacing in a rate responsive, atrial based pacing mode comprises varying pacing rate responsive to minute ventilation.

16. The method of claim 13, wherein delivering cardiac pacing in a rate responsive, atrial based pacing mode comprises varying pacing rate responsive to blood oxygen.

17. The method of claim 13, wherein delivering cardiac pacing in a rate responsive, atrial based pacing mode comprises varying pacing rate responsive to movement.

18. The method of claim 13, wherein delivering cardiac pacing in a rate responsive, atrial based pacing mode comprises varying pacing rate responsive to activity.

19. The method of claim 13, wherein delivering cardiac pacing in a rate responsive, atrial based pacing mode comprises varying pacing rate responsive to a chemical level.

20. The method of claim 13, wherein delivering cardiac pacing in a rate responsive, atrial based pacing mode comprises varying pacing rate responsive to a blood gas saturation level.

* * * * *